United States Patent [19]

Dudney

[11] Patent Number: 5,616,318

[45] Date of Patent: Apr. 1, 1997

[54] **USE OF *XENORHABDOUS NEMATOPHILUS* IM/1 AND 19061/1 FOR FIRE ANT CONTROL**

[76] Inventor: Ralph A. Dudney, 10803 W. Hidden Lakes La., Richmond, Tex. 77469

[21] Appl. No.: 488,820

[22] Filed: Jun. 9, 1995

[51] Int. Cl.$^6$ .................................................. A01N 63/00
[52] U.S. Cl. ...................... 424/93.1; 424/93.7; 424/405
[58] Field of Search .................. 424/93.1, 93.7, 424/405

[56] References Cited

U.S. PATENT DOCUMENTS

| | | |
|---|---|---|
| 4,672,130 | 6/1987 | Rhodes et al. ........................... 548/453 |
| 4,837,222 | 6/1989 | Gregson et al. ........................ 514/422 |
| 5,445,819 | 8/1995 | Smart, Jr. et al. ..................... 424/93.1 |
| 5,466,448 | 11/1995 | Smart, Jr. et al. .................... 424/93.1 |

*Primary Examiner*—John C. Bleutge
*Assistant Examiner*—Robert H. Harrison
*Attorney, Agent, or Firm*—William J. Beard

[57] ABSTRACT

Liquid cultures of bacteria of the genus XENORHABDOUS strains NEMATOPHILUS Im/1 and 19061/1 made up on LB broth and cultured for up to 24 hours and applied directly to mounds of the imported fire ant SOLENOPSIS INVICTA have been found effective in killing the pest. The liquid cultures are applied in a density of about $1 \times 10^7$ bacteria per ml by either low pressure spray, high pressure spray or pouring directly on the mounds.

14 Claims, No Drawings

5,616,318

USE OF *XENORHABDOUS NEMATOPHILUS* IM/1 AND 19061/1 FOR FIRE ANT CONTROL

BACKGROUND OF THE INVENTION

The red imported fire ant, SOLENOPSIS INVICTA, was accidentally introduced into the United States from South America in the 1920's via Mobile, Ala. Since then its habitat has spread across all of the Southern United States as far west as presently near the Pecos River valley in Texas and to the Atlantic Ocean on the east. It ranges from the Gulf of Mexico as far north as Tennessee and North Carolina. This pest is very aggressive and has largely replaced native North American fire ants in the areas it infests.

SOLENOPSIS INVICTA can sting repeatedly and will attack anything that disturbs its nests or mounds or its food sources. Symptoms of a sting inflicted on humans include burning and itching. The venom which is injected can cause a white pustule to form in a day or two which can leave permanent scars. The stings are not usually life threatening but multiple stings can cause secondary infections and, in sensitive persons, can cause chest pains or nausea.

Attempts to chemically control SOLENOPSIS INVICTA in the 1960's, 70's and 80's used chemicals which also destroyed native ant species and may have actually aided the spread of these pests. Chemicals provide only temporary control of the ants and must be reapplied periodically for as long as control is desired. The application of chemical controls over long time periods can have other undesired side effects if the applications are cumulative. Because of these and other problems associated with chemical control, it would be highly desirable to control SOLENOPSIS INVICTA by use of a biological agent which would be essentially harmless to mammals and to other desirable insect species.

It has been known that effective control of some insect species, such as fleas, may be obtained by the use of nematodes. In particular some commercial nematode preparations are offered for this purpose such as BIOSAFE, made by the Solaris Group of San Ramon, Calif. and BIO FLEA HALT made by Farnum Pet Products of Phoeniz, Ariz. Nematodes of the families STEINERNEMATIDAE are symbiotically associated with bacteria of the genus XENORHABDUS. However, a study of the response of SOLENPOSIS INVICTA by Drees et al (Journal of Economic Entomology 85(2); 365–370; 1992) to nematode treatment in the field which included drenching SOLENPOSIS INVICTA mounds with solutions (of about $10^6$ nematodes per mound) of STEINERNEMA and HETEROHABDITIS NEMATODES showed that such drenching primarily caused relocation of the SOLENOPSIS INVICTA to satellite mounds in the vicinity. This same study showed, however, that under laboratory conditions SOLENOPSIS INVICTA larvae were moderately (78–100%) susceptible to infection by each nematode species tested in high dose ranges ($10^5$ nematodes per sample dish) and by a lesser amount (38–88%) in lower dose ranges ($10^3$ nematodes per sample dish). Also noted was that in the higher dose ranges more than 20% of the worker ant SOLENOPSIS INVICTA died, although these ants were shown not to be susceptible direct infection by the nematodes. Moreover, the use of the nematodes as a vector for infection by the bacteria limits the shelf of life of the control product to that of the nematode host, a matter of a few weeks.

It has been known that anitbiotics possessing antibacterial, antifungal, anti-inflammatory and antiulcerogenic properties can be derived from cultures of bacteria of the genus XENORHABDUS. For example, such compounds and their uses are disclosed in U.S. Pat. Nos. 4,837,222 and 4,672,130. However, experimentation done previously has been suggestive that the nematode host of the XENORHABDUS was necessary to introduce the bacteria into the system of a target animal as it was believed that XENORHABDUS did not survive well in soil or water and were not pathogenic for insects when ingested. See ENTOMOPATHOGENIC NEMATODES IN BIOLOGICAL CONTROL, CRC Press, Boca Raton, Fla.,1990, Chapter 4, pp. 75–89.

SUMMARY OF THE INVENTION

Recent experiments using at least two different strains of the genus XENORHABDUS SPECIES NEMATOPHILUS directly applied to SOLENOPSIS INVICTA colonies have been successful in causing immobilization and death of the colonies. The XENORHABDUS species employed for these experiments were cultured from samples supplied by Washington State University. The cultured bacteria were stored at low temperature for several months and found to be still active enough to be effective. Culture concentrate can be diluted with distilled water or non-chlorinated well water to bring the concentrate to practical field usage level.

DETAILED DESCRIPTION OF THE INVENTION AND ITS PREFERRED EMBODIMENTS

Several strains of the species XENORHABDUS are available from the American Type Culture Collection (ATCC). Samples of two strains of XENORHABDUS NEMATOPHILUS, strain 19061/1 and strain Im/1 were obtained from Washington State University. Strain 19061/1 is an ATCC strain. Strain Im/1 is designated ATCC 55858, a deposit being made on Oct. 25, 1996 at the American Type Culture Collection, Rockville, Md. And is identified therein as XENORHABDUS NEMATOPHILUS Im-1 or Im/1 (phase 1) under this ATCC Designation. Strain Im/1 can be isolated from its nematode host STEINERAMA CAPRECAPSAE A11-25 by streaking the macerated, surface sterilized nematodes onto NBTA medium, as described by Xu et al (Applied Environmental Micriobiology, April 1989, pp. 806–812).

Stock cultures of both strains were established on nutrient agar and LB agar and preserved at −80° C. The stock cultures are maintained by monthly transfers.

To obtain enough bacteria for experimentation, samples of stock culture were cultured on LB broth having the composition (per liter) of 10 grams Triptone, 5 grams technical grade yeast, and 10 grams sodium chloride. The LB broth culture was made in Fernbach flasks shaken slowly at 60–90 RPM at 30° C. for from 21–24 hours.

EXPERIMENT 1—EFFECT OF 19061/1 and Im/1 XENORHABDUS NEMATOPHILUS ON SOLENOPSIS INVICTA COLONIES

Example 1

Day 1—Approximately one liter of LB broth cultured 19061/strain and Im/1 strain were poured on four separate large SOLENOPSIS INVICTA colonies (mounds) two each.

Day 2—Mounds inspected—No apparent effect.

Day 5—Mounds inspected—Some small amount of ant activity in mounds treated with strain 19061/1. No ant activity at all in mounds treated with strain Im/1.

Example 2

Day 1—Approximately one liter of LB broth cultured 19061/1 strain and LB broth cultured Im/1 strain were poured on four separate large mounds. These were all cultured for 48 hours on the LB broth (shaken) rather than 24 hours as in the previous example.

Day 2—Mounds inspected—No apparent effect.

Day 5—Mounds inspected—Slight ant activity in mounds treated with 19061/1 strain. There was no activity in mounds treated with Im/1 strain. However, both Im/1 and 19061/1 strain appear less effective than in Example 1.

Example 3

Day 1—Approximately one liter of LB broth cultured 19061/1 strain and Im/1 strain as in Example 1 were poured on 4 separate mounds. These cultures were still cultures as opposed to shaken cultures as in Example 1.

Day 2—Mounds inspected—No apparent effect.

Day 5—Mounds inspected—Slight ant activity left in all mounds, but much reduced. The still cultures of both 19061/1 and Im/1 appear not as effective as the shaken cultures.

Example 4

Day 1—Approximately one liter of LB broth cultured 19061/1 and Im/1 strains were poured on four separate large mounds, however the 24 hour shaken cultures were held still for three hours at ambient temperature prior to application.

Day 2—Mounds inspected—No apparent effect.

Day 5—Mounds inspected—Significantly reduced ant activity in all mounds, but does not appear as effective as in prior examples where freshen (no delay) broth applied to mounds.

EXPERIEMENT 2—FULL SCALE FIELD TRIALS ON XENORHABDUS NEMATOPHILUS Im/1 STRAIN ON SOLENOPSIS INVICTA MOUNDS IN INFESTED ACREAGE

Example 1

Site approximately 7.5 acres of open ground and evergreen (pine) forested, surrounded by open fields which are heavily infested with SOLENOPSIS INVICTA, and which is itself heavily infested with SI. A large number of SI mounds (244) essentially in an open area covering approximately 2 acres were chosen and flagged for the test. Each mound was visually inspected and found to be very active with the SI.

Twenty gallons of LB broth were inoculated with cultures of Im/1 strain containing approximately $6.9 \times 10^7$ bacetria/mL for a total of approximately $6.4 \times 10^{10}$ bacteria in the 20 gallon culture. The culture was incubated at 82° F. for about 24 hours prior to application to the selected mounds with occasional agitation.

Day 1—For spraying onto the selected mounds the just described culture was diluted approximately 1:50 with unchlorinated well water. This produced a spray mixture having a concentration of about $1 \times 10^7$ bacteria per mL. Weather was sunny and warm 85° F.

Four separate applications were done each with 0.5 gallons of culture to 25 gallons of well water (1:50 dilution). In the first application 18 mounds were treated with a gentle hose like flood for an average of 1.4 gallons/mound. Applications 2, 3 and 4 were conducted with a strong spray directed into the mounds which physically tore apart the mounds. Within one hour after the spraying the ants were observed to be rebuilding the mounds. The four applications are summarized in Table I below.

TABLE 1

| Application No. | Mounds Treated per 25 gallons | Gallons per mound | Bacteria per mound |
|---|---|---|---|
| 1 | 18 | 1.4 | $5.3 \times 10^{10}$ |
| 2 | 85 | 0.29 | $1.1 \times 10^{10}$ |
| 3 | 79 | 0.32 | $1.2 \times 10^{10}$ |
| 4 | 62 | 0.40 | $1.5 \times 10^{10}$ |

Day 4—A sudden temperature change to daily highs in the 50° F. range occurred the day after application. No visible effect from the spraying was observed on any of the 244 mounds flagged and inspected.

Day 25—The 244 mounds were inspected and approximately 30% of mounds treated by pressure spray were dead or inactive. Daily temperatures starting to rise into mid 70° F. range.

Day 45—The 244 mounds were inspected and about 70% appeared to have no ant activity therein. Temperatures has been in upper 70° F. to lower 80° F. range at mid-day since last observation.

Day 50—The 244 mounds inspected and only eleven (11) showed any ant activity. This represents a 94.5% kill ratio. Weather has gotten warmer, now averaging mid 80° F. range at mid-day.

Example 2

Day 1—Mixed up approximately two gallons of the concentrated XENORHABDUS NEMATOPHILUS Im/1 culture which has been frozen for about 4 months at 0° F. by adding 0.5 pint culture to 2 gallons unchlorinated well water with (1:32 dilution). The frozen culture was air thawed to ambient temperature (75° F.) and mixed with the unchlorinated well water at ambient temperature and applied via low pressure spray to six (6) mounds of SOLENOPSIS INVICTA in a 0.5 acre space of open ground.

Day 2—Sprayed SI mounds inspected and no apparent diminution in ant activity observed. Air temperature about 85° F. at mid-day.

Day 3—No ant activity at all in 4 of the 6 treated mounds. Slight but highly diminished ant activity (about 10% of that at application) observed in 2 of the treated mounds. Air temperature about 85° F. at mid-day.

Day 5—All six treated mounds completely devoid of any ant activity. Air temperature average mid 80° F. range at mid-day during experiment.

Example 3

Day 1—Sixty seven (67) SI mounds in a different 1 acre portion of the same 7.5 acre tract treated with spray diluted 1:50 from the same same as that applied in Example 1 of this field experiment. Temperature ranging into mid 80° F. range at mid day, down to upper 60° F. range at night at time of application. Approximately $1 \times 10^{10}$ bacteria per mound produced in the treatment.

Day 2—67 SI mounds inspected—no apparent effect from spraying.

Day 5—67 SI mounds inspected—ant activity present in only 2 of the treated mounds. All other mounds appear dead.

The experiments described above illustrate the effectiveness of the direct application of bacteria of the genus XENORHABDUS species nematophilus in controlling or destroying fire ant populations of SOLENOPSIS INVICTA in the field. Application of the bacteria appear to be affected by the air and soil ambient temperature during and following the application. The XENORHABDUS bacteria do appear to survive in the soil for a matter of weeks in a dormant state in cooler temperature in the range of 50° F. to 60° F. They can become active again as temperatures of air and soil increase after their dormant period to a range of 80° F. to 90° F.

I claim:

1. A method for treating fire ants of the species SOLENOPSIS INVICTA with a bacteriological agent comprising the steps of:

preparing a liquid culture of bacteria of the genus XENORHABDOUS species NEMATOPHILUS strain 19061/1 by inoculating a culture medium of LB broth with a stock culture of said strain and incubating for a period of up to 24 hours; and applying an insecticidally effective amount of said liquid culture of bacteria onto a mound of ants.

2. The method of claim 1 wherein said liquid culture has a population of about $1 \times 10^7$ bacteria per mL and is applied in an amount sufficient to at least wet the mound.

3. The method of claim 1 wherein said liquid culture is applied by a high pressure spray.

4. The method of claim 1 wherein said liquid culture is applied by a low pressure spray.

5. The method of claim 1 wherein the application of said liquid culture is performed with ambient temperature in the range between 70° F. to 90° F.

6. The method of claim 5 wherein the ambient temperature are in the range of 75° F. to 85° F.

7. The method of claim 1 wherein the application of said liquid culture applies an amount of at least about $1 \times 10^{10}$ bacteria per mound treated.

8. A method for treating fire ants of the species SOLENOPSIS INVICTA with a bacteriological agent comprising the steps of:

preparing a liquid culture of bacteria of the genus XENORHABDOUS species NEMATOPHILUS strain Im/1 by inoculating a culture of LB broth with a stock culture of said strain and incubating for a period of up to 24 hours; and applying an insecticidally effective amount of said liquid culture of bacteria onto a mound of ants.

9. the method of claim 8 wherein said liquid culture has a population of about $1 \times 10^7$ bacteria per ml and is applied in an amount sufficient to at least wet the mound.

10. The method of claim 8 wherein said liquid culture is applied by a high pressure spray.

11. The method of claim 8 wherein said liquid culture is applied by low pressure spray.

12. The method of claim 8 wherein the application of said liquid culture is performed with ambient temperature in the range of 70° F. to 90° F.

13. The method of claim 14 wherein the ambient temperature is in the range 70° F. to 85° F.

14. The method of claim 14 wherein the application of said liquid culture applies an amount of at least about $1 \times 10^{10}$ bacteria per mound treated.

* * * * *